United States Patent
Chen et al.

(10) Patent No.: US 10,203,387 B2
(45) Date of Patent: Feb. 12, 2019

(54) MR IMAGING WITH ENHANCED SUSCEPTIBILITY CONTRAST

(71) Applicant: KONINKLIJKE PHILIPS N.V., Eindhoven (NL)

(72) Inventors: Zhaolin Chen, Eindhoven (NL); Miha Fuderer, Eindhoven (NL); Elizabeth Anne Moore, Eindhoven (NL); Gwenael Herigault, Eindhoven (NL); Kim Van De Ven, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 431 days.

(21) Appl. No.: 14/895,242

(22) PCT Filed: Jun. 5, 2014

(86) PCT No.: PCT/EP2014/061814
§ 371 (c)(1),
(2) Date: Dec. 2, 2015

(87) PCT Pub. No.: WO2014/195454
PCT Pub. Date: Dec. 11, 2014

(65) Prior Publication Data
US 2016/0116560 A1 Apr. 28, 2016

(30) Foreign Application Priority Data
Jun. 6, 2013 (EP) .................................. 13170814

(51) Int. Cl.
*A61B 5/00* (2006.01)
*A61B 5/055* (2006.01)
(Continued)

(52) U.S. Cl.
CPC ........ *G01R 33/5602* (2013.01); *A61B 5/0042* (2013.01); *A61B 5/055* (2013.01);
(Continued)

(58) Field of Classification Search
CPC ................ G01R 33/5602; G01R 33/36; G01R 33/3852; G01R 33/556; G01R 33/5608; G01R 33/5615; G01R 33/5616
See application file for complete search history.

(56) References Cited

U.S. PATENT DOCUMENTS 6,658,280 B1 12/2003 Haacke
8,829,902 B2 9/2014 Yoneda et al.
(Continued)

FOREIGN PATENT DOCUMENTS

JP 2010158459 A 7/2010

*Primary Examiner* — Rodney A Bonnette

(57) ABSTRACT

An object (10) in an examination volume of a MR device (1) is imaged with improved susceptibility weighted contrast. The imaging includes the steps of: a) generating at least two echo signals at different echo times by subjecting the object (10) to an imaging sequence of RF pulses and switched magnetic field gradients; b) acquiring the echo signals; c) repeating steps a) and b) for a plurality of phase encoding steps; d) reconstructing an intermediate MR image for each echo time from the acquired echo signals; and e) generating a susceptibility weighted MR image by computing, for each voxel of the susceptibility weighted MR image, a non-linear combination of the voxel values of the intermediate MR images at the respective image position. The non-linear combination emphasizes lower voxel magnitude values more than higher voxel magnitude values.

19 Claims, 3 Drawing Sheets

(51) Int. Cl.
  *G01R 33/36*   (2006.01)
  *G01R 33/56*   (2006.01)
  *G01R 33/385*  (2006.01)
  *G01R 33/561*  (2006.01)

(52) U.S. Cl.
  CPC ......... *G01R 33/36* (2013.01); *G01R 33/3852* (2013.01); *G01R 33/56* (2013.01); *G01R 33/5608* (2013.01); *G01R 33/5615* (2013.01); *G01R 33/5616* (2013.01)

(56) References Cited

U.S. PATENT DOCUMENTS

| | | | |
|---|---|---|---|
| 2009/0251140 A1* | 10/2009 | Bhardwaj | G01R 33/5615 324/307 |
| 2010/0022869 A1 | 1/2010 | Kimura | |
| 2010/0142785 A1 | 6/2010 | Dahnke et al. | |
| 2010/0142789 A1* | 6/2010 | Chang | A61B 5/055 382/131 |
| 2010/0277172 A1 | 11/2010 | Takizawa | |
| 2011/0275926 A1 | 11/2011 | Du | |
| 2012/0046539 A1* | 2/2012 | Visser | G01R 33/5602 600/410 |
| 2012/0326721 A1* | 12/2012 | Remmele | G01R 33/50 324/309 |
| 2014/0043022 A1* | 2/2014 | Geerts-Ossevoort | G01R 33/4828 324/306 |

\* cited by examiner a)  b)

MR IMAGING WITH ENHANCED SUSCEPTIBILITY CONTRAST

CROSS REFERENCE TO RELATED APPLICATIONS

This application is a U.S. national phase application of International Application No. PCT/EP2014/061814, filed on Jun. 6, 2014, which claims the benefit of EP Application Serial No. 13170814.1 filed on Jun. 6, 2013 and is incorporated herein by reference.

FIELD OF THE INVENTION

The invention relates to the field of magnetic resonance (MR) imaging. It concerns a method of MR imaging of an object placed in the examination volume of a MR device. The invention also relates to a MR device and to a computer program to be run on a MR device.

BACKGROUND OF THE INVENTION

Image-forming MR methods which utilize the interaction between magnetic fields and nuclear spins in order to form two-dimensional or three-dimensional images are widely used nowadays, notably in the field of medical diagnostics, because for the imaging of soft tissue they are superior to other imaging methods in many respects, do not require ionizing radiation and are usually not invasive.

SUMMARY OF THE INVENTION

According to the MR method in general, the body of the patient to be examined is arranged in a strong, uniform magnetic field $B_0$ whose direction at the same time defines an axis (normally the z-axis) of the co-ordinate system on which the measurement is based. The magnetic field $B_0$ produces different energy levels for the individual nuclear spins in dependence on the magnetic field strength which can be excited (spin resonance) by application of an electromagnetic alternating field (RF field) of defined frequency (so-called Larmor frequency, or MR frequency). From a macroscopic point of view, the distribution of the individual nuclear spins produces an overall magnetization which can be deflected out of the state of equilibrium by application of an electromagnetic pulse of appropriate frequency (RF pulse) while the magnetic field $B_0$ extends perpendicular to the z-axis, so that the magnetization performs a precessional motion about the z-axis. The precessional motion describes a surface of a cone whose angle of aperture is referred to as flip angle. The magnitude of the flip angle is dependent on the strength and the duration of the applied electromagnetic pulse. In the case of a so-called 90° pulse, the spins are deflected from the z axis to the transverse plane (flip angle 90°).

After termination of the RF pulse, the magnetization relaxes back to the original state of equilibrium, in which the magnetization in the z direction is built up again with a first time constant $T_1$ (spin lattice or longitudinal relaxation time), and the magnetization in the direction perpendicular to the z direction relaxes with a second time constant $T_2$ (spin-spin or transverse relaxation time). The variation of the magnetization can be detected by means of receiving RF coils which are arranged and oriented within an examination volume of the MR device in such a manner that the variation of the magnetization is measured in the direction perpendicular to the z-axis. The decay of the transverse magnetization is accompanied, after application of, for example, a 90° pulse, by a transition of the nuclear spins (induced by local magnetic field inhomogeneities) from an ordered state with the same phase to a state in which all phase angles are uniformly distributed (dephasing). The dephasing can be compensated by means of a refocusing pulse (for example a 180° pulse). This produces an echo signal (spin echo) in the receiving coils.

In order to realize spatial resolution in the body, linear magnetic field gradients extending along the three main axes are superposed on the uniform magnetic field $B_0$, leading to a linear spatial dependency of the spin resonance frequency. The signal picked up in the receiving coils then contains components of different frequencies which can be associated with different locations in the body. The signal data obtained via the receiving coils corresponds to the spatial frequency domain and is called k-space data. The k-space data usually includes multiple lines acquired with different phase encoding. Each line is digitized by collecting a number of samples. A set of k-space data is converted to an MR image by means of Fourier transformation.

In MR imaging, the selection of a particular imaging sequence determines the relative appearance of different tissue types in the resultant MR images. Various properties of tissue may be used to create MR images with a desirable contrast between different tissues. $T_2^*$ or susceptibility weighted contrast arises from local inhomogeneities of the magnetic field among tissues. $T_2^*$ weighted contrast may be used for a number of applications including, but not limited to, enhanced detection of stroke and hemorrhage, tumors, micro-hemorrhages in trauma patients and occult vascular diseases, and for applications such as separating arteries and veins, imaging of venous vascular networks and assessing iron buildup in neurodegenerative diseases. Susceptibility differences between body tissues can be utilized as a type of contrast in MR imaging that is different from other types of contrast, like in spin density, $T_1$-, or $T_2$-weighted imaging. Signals from substances with different magnetic susceptibilities compared to their neighboring tissue will become out of phase with the neighboring tissue at sufficiently long echo times. On this basis, Haacke et al. (U.S. Pat. No. 6,658,280 B1) have demonstrated that phase imaging offers a means of enhancing contrast in MR imaging. Specifically, the phase images themselves can provide contrast between gray matter (GM) and white matter (WM) in brain imaging, iron-laden tissues, venous blood vessels, and other tissues with susceptibilities that are different from the background tissue. In particular, image contrast between blood vessels and surrounding tissue can be achieved on the basis of the phase difference between MR signals from blood and tissue caused by differences in susceptibility. In the approach of Haacke et al., magnitude and phase images are combined. The phase images are high-pass-filtered and then transformed to a special phase mask that varies in amplitude between zero and unity. This mask is multiplied an integer number of times into the original magnitude image to create enhanced contrast between tissues with different susceptibilities. An alternative approach has been proposed by Bhardwaj et al. (US 2009/0251140 A1), wherein a susceptibility weighted image is generated by combining image data acquired at different echo times based on the application of a weighting function.

It is an object of the invention to provide a method of MR imaging with improved susceptibility weighted contrast.

In accordance with the invention, a method of MR imaging of an object positioned in the examination volume of a MR device is disclosed. The method comprises the steps of:

a) generating at least two echo signals at different echo times by subjecting the object to an imaging sequence of RF pulses and switched magnetic field gradients;
b) acquiring the echo signals;
c) repeating steps a) and b) for a plurality of phase encoding steps;
d) reconstructing an intermediate MR image for each echo time from the acquired echo signals; and
e) generating a susceptibility weighted MR image by computing, for each voxel of the susceptibility weighted MR image, a non-linear combination of the voxel values of the intermediate MR images at the respective image position, wherein the non-linear combination emphasizes lower voxel magnitude values more than higher voxel magnitude values.

In accordance with the invention, at least two independent MR signal data sets are acquired, wherein each MR signal data set comprises the echo signals acquired at one echo time value. In other words, each MR signal data set is attributed to one of two or more echo time values. An intermediate MR image is reconstructed from each MR signal data set such that each intermediate MR image is attributed to the respective echo time value. The susceptibility weighted image is obtained by combining the intermediate MR images in a specific non-linear fashion. According to the invention, a voxel-wise non-linear combination of the echo data is formed in such a way that the lowest signal amplitudes are emphasized. This means, in other words, that the non-linear combination translates the lower signal amplitudes in the intermediate MR images into a larger contribution to the susceptibility weighted image, while the higher signal amplitudes are translated into a smaller contribution to the susceptibility weighted image.

In one possible embodiment, the reciprocal values of the voxel values of the intermediate MR images are computed and the resulting values are combined for each image position. The invention thereby achieves improved susceptibility weighted contrast even between small blood vessels and surrounding tissue. Notably, noise in the MR signals from surrounding tissue is reduced by effective averaging. In voxels that (partially) contain a blood vessel, amplitude reduction due to partial volume effect is enhanced.

In a preferred embodiment of the invention, the step of generating the susceptibility weighted MR image comprises:
computing the absolute values of the voxel values of each intermediate image at each image position;
computing the reciprocal values by raising each absolute value to a negative exponent, which may be integer or non-integer;
adding up, for each voxel of the susceptibility weighted MR image, the reciprocal values at the respective image position. It is essential in this embodiment that the echo data is inverted first and then combined at each voxel position. Further weighting factors may be applied when computing the sum of reciprocal values. Moreover, the combination of the reciprocal values at each image position should be normalized. This concept yields particular emphasis on low-intensity echo signal data, i.e. susceptibility contrast.

The intermediate MR images of the method of the invention may be magnitude images or susceptibility enhanced magnitude images or complex images.

In order to obtain an optimal susceptibility contrast it is advantageous to apply the echo combination technique of the invention to already susceptibility enhanced intermediate MR image data. To this end, the intermediate MR images may be acquired, e.g., by using the known phase difference enhanced imaging (PADRE) concept (WO 2010/073923 A1).

In case the intermediate images are complex images, the non-linear combination may involve the computation of a weighted sum, wherein larger weighting factors are applied to voxel values of the intermediate images having a lower magnitude, while smaller weighting factors are applied to voxel values of the intermediate images having a higher magnitude. In this way, the resulting susceptibility weighted MR image can be generated as a complex image (with preserved phase information).

In a further preferred embodiment of the invention, the imaging sequence used for generating and acquiring the echo signals is a multi-echo gradient echo sequence. In other words, the two or more echo signals are generated as gradient echoes by appropriate switching of magnetic field gradients. Since gradient echoes do not refocus effects of main magnetic field inhomogeneity, gradient echo sequences are known to be inherently sensitive to susceptibility effects. A multi-echo sequence enables acquisition of the required signal data within a short scan time.

The method of the invention described thus far can be carried out by means of a MR device including at least one main magnet coil for generating a uniform, steady magnetic field $B_0$ within an examination volume, a number of gradient coils for generating switched magnetic field gradients in different spatial directions within the examination volume, at least one RF coil for generating RF pulses within the examination volume and/or for receiving MR signals from an object positioned in the examination volume, a control unit for controlling the temporal succession of RF pulses and switched magnetic field gradients, and a reconstruction unit for reconstructing MR images from the received MR signals. The method of the invention can be implemented by a corresponding programming of the reconstruction unit and/or the control unit of the MR device.

The method of the invention can be advantageously carried out on most MR devices in clinical use at present. To this end it is merely necessary to utilize a computer program by which the MR device is controlled such that it performs the above-explained method steps of the invention. The computer program may be present either on a data carrier or be present in a data network so as to be downloaded for installation in the control unit of the MR device.

BRIEF DESCRIPTION OF THE DRAWINGS

The enclosed drawings disclose preferred embodiments of the present invention. It should be understood, however, that the drawings are designed for the purpose of illustration only and not as a definition of the limits of the invention. In the drawings.

DETAILED DESCRIPTION OF THE EMBODIMENTS

Figure 1:
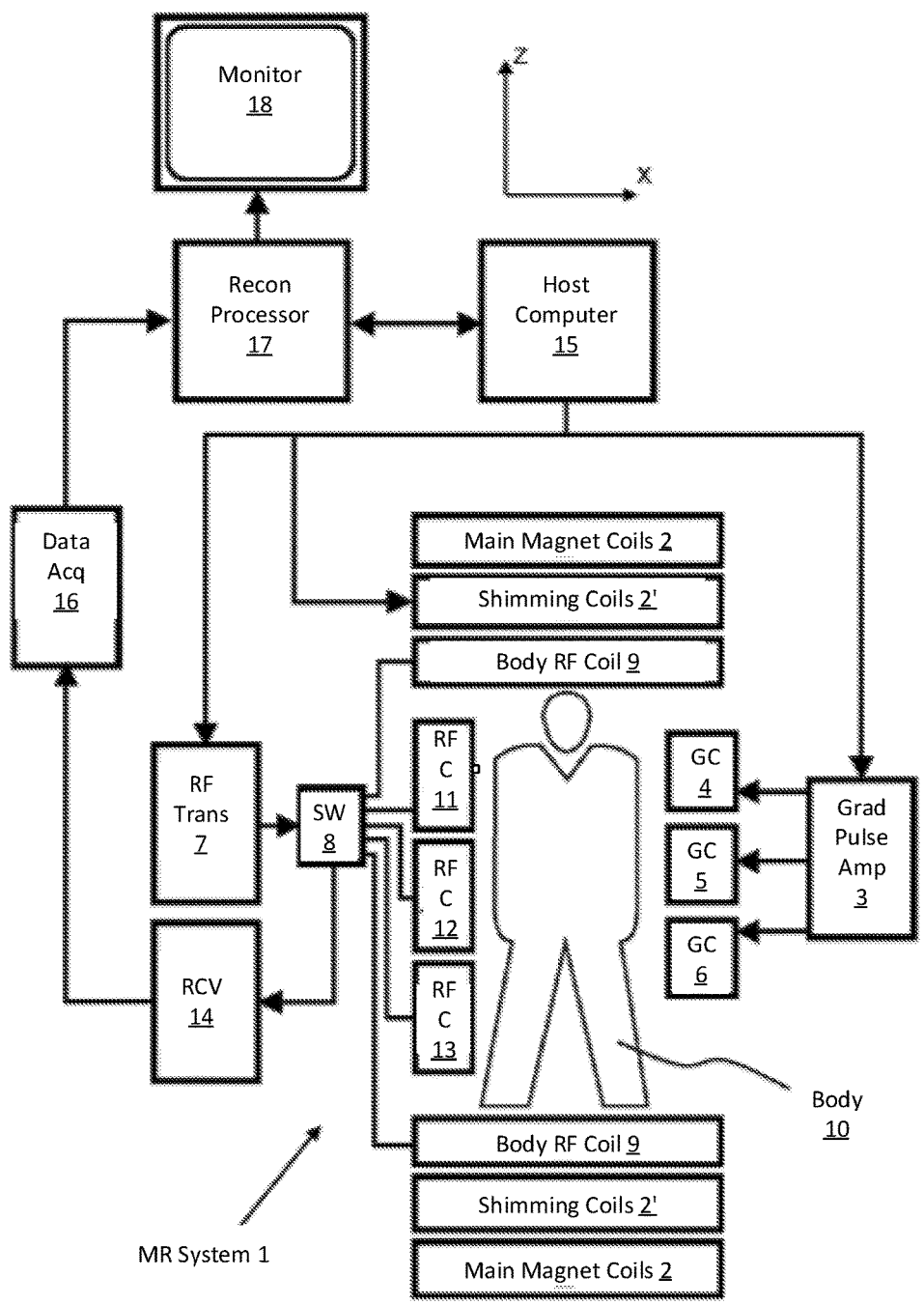
FIG. 1 shows a MR device for carrying out the method of the invention.

With reference to FIG. 1, a MR device 1 is shown. The device comprises superconducting or resistive main magnet coils 2 such that a substantially uniform, temporally constant main magnetic field $B_0$ is created along a z-axis through an examination volume. The device further comprises a set of ($1^{st}$, $2^{nd}$, and—where applicable—$3^{rd}$ order) shimming coils 2', wherein the current flow through the individual shimming coils of the set 2' is controllable for the purpose of minimizing $B_0$ deviations within the examination volume.

A magnetic resonance generation and manipulation system applies a series of RF pulses and switched magnetic field gradients to invert or excite nuclear magnetic spins, induce magnetic resonance, refocus magnetic resonance, manipulate magnetic resonance, spatially and otherwise encode the magnetic resonance, saturate spins, and the like to perform MR imaging.

More specifically, a gradient pulse amplifier 3 applies current pulses to selected ones of whole-body gradient coils 4, 5 and 6 along x, y and z-axes of the examination volume. A digital RF frequency transmitter 7 transmits RF pulses or pulse packets, via a send-/receive switch 8, to a body RF coil 9 to transmit RF pulses into the examination volume. A typical MR imaging sequence is composed of a packet of RF pulse segments of short duration which, together with any applied magnetic field gradients, achieve a selected manipulation of nuclear magnetic resonance. The RF pulses are used to saturate, excite resonance, invert magnetization, refocus resonance, or manipulate resonance and select a portion of a body 10 positioned in the examination volume. The MR signals are also picked up by the body RF coil 9.

For generation of MR images of limited regions of the body 10 by means of parallel imaging, a set of local array RF coils 11, 12, 13 are placed contiguous to the region selected for imaging. The array coils 11, 12, 13 can be used to receive MR signals induced by body-coil RF transmissions.

The resultant MR signals are picked up by the body RF coil 9 and/or by the array RF coils 11, 12, 13 and demodulated by a receiver 14 preferably including a preamplifier (not shown). The receiver 14 is connected to the RF coils 9, 11, 12 and 13 via send-/receive switch 8.

A host computer 15 controls the shimming coils 2' as well as the gradient pulse amplifier 3 and the transmitter 7 to generate MR imaging sequences, such as fast field echo (FFE) imaging, and the like. For the selected sequence, the receiver 14 receives a single or a plurality of MR data lines in rapid succession following each RF excitation pulse. A data acquisition system 16 performs analog-to-digital conversion of the received signals and converts each MR data line to a digital format suitable for further processing. In modern MR devices the data acquisition system 16 is a separate computer which is specialized in acquisition of raw image data.

Ultimately, the digital raw image data are reconstructed into an image representation by a reconstruction processor 17 which applies a Fourier transform or other appropriate reconstruction algorithms. The MR image may represent a planar slice through the patient, an array of parallel planar slices, a three-dimensional volume, or the like. The image is then stored in an image memory where it may be accessed for converting slices, projections, or other portions of the image representation into appropriate format for visualization, for example via a video monitor 18 which provides a man-readable display of the resultant MR image.

Figure 3:
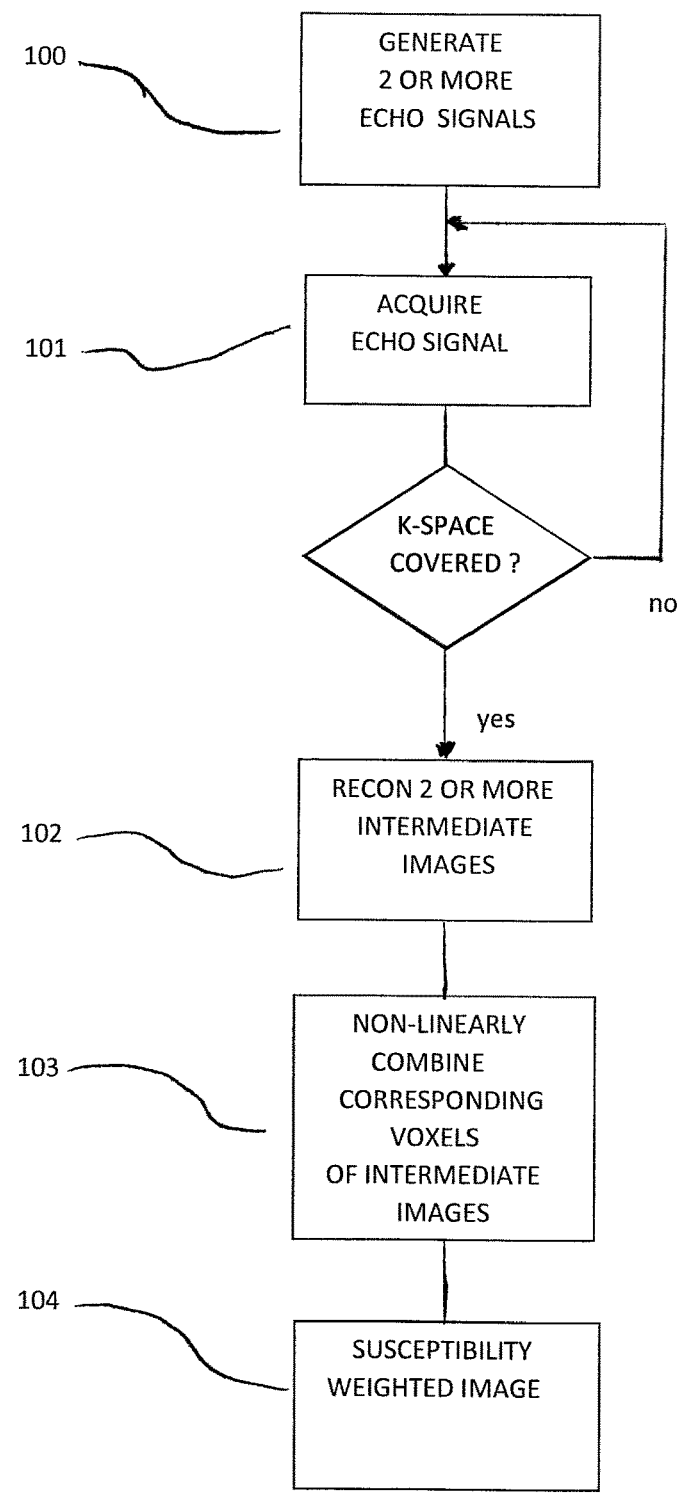
FIG. 3 shows steps carried out by the MR device in accordance with the present invention.

With reference to FIG. 3, in a step 100, two or more echo signals are generated by means of a multi-echo gradient imaging sequence at two different echo times. In a step 101, the echo signals are acquired for a plurality of phase encoding steps in order to cover k-space appropriately. In a step 102, an intermediate MR image is reconstructed for each echo time value from the acquired echo signals. This means that a first intermediate MR image is reconstructed from the echo signals acquired at a first echo time value, a second intermediate MR image is reconstructed from the echo signals acquired at a second echo time value, and so on. In a step 103, a susceptibility weighted MR image 104 is computed by computing, for each voxel of the susceptibility weighted MR image, a non-linear combination of the voxel values of the intermediate MR images at the respective image position. This is done in such a fashion that lower voxel values (corresponding to lower MR signal amplitudes) are given more emphasis in the resulting susceptibility weighted MR image than higher voxel values (corresponding to higher MR signal amplitudes).

The method of the invention provides improved susceptibility contrast vis-à-vis the prior art. The method of the invention can be applied to magnitude images, complex images and susceptibility enhanced magnitude images (such as, e.g., PADRE images).

In one embodiment, the intensities of each voxel of the intermediate MR images are first inverted and then combined into the susceptibility weighted MR image. Finally, the combined data is normalized. According to this embodiment, several examples are given in the following:

$$I = \sqrt[-p]{\frac{1}{N}\sum_{i=1}^{N}\|S_i\|^{-p}} \tag{1}$$

Therein, I is a voxel value of the susceptibility weighted MR image at a given image position, N is the total number of echo time values, and $S_i$ represents the voxel values in the intermediate MR images attributed to the i-th echo value at the respective image position. The exponent p fulfills the relation p>0, wherein p can be any integer or non-integer value.

In another embodiment, the following formula may be used:

$$I = \frac{\sum_{i=1}^{N}\|S_i\|^{-p}}{\sum_{i=1}^{N}\|S_i\|^{-(p+1)}}, p > 0. \tag{2}$$

Another formula for computing the susceptibility weighted MR image is:

$$I = -\ln\left(\frac{1}{N}\sum_{i=1}^{N}\exp(-\|S_i\|)\right) \tag{3}$$

In another embodiment, the voxel-wise non-linear combination of the acquired echo signal data with emphasis on low intensity echo signal data can be computed by using one of the following formulas:

$$\frac{\sum_{i=1}^{N}\frac{S_i}{\|S_i\|^p}}{\sum_{i=1}^{N}\|S_i\|^{-p}}, p \tag{4a}$$

or $$I = \frac{\sum_{i=1}^{N}S_i * \exp(-\|S_i\|)}{\sum_{i=1}^{N}\exp(-\|S_i\|)}. \tag{4b}$$

The latter two formulas may be used in case the intermediate images are complex images. The non-linear combination involves the application of weighting factors ($1/\|S_i\|^p$ or $\exp(-\|S_i\|)$), such that larger weighting factors are used for voxel values $S_i$ having a lower magnitude $\|S_i\|$, while smaller weighting factors are used for voxel values $S_i$ having a higher magnitude $\|S_i\|$. In this way, the resulting susceptibility weighted MR image I is also a complex image.

Figure 2:
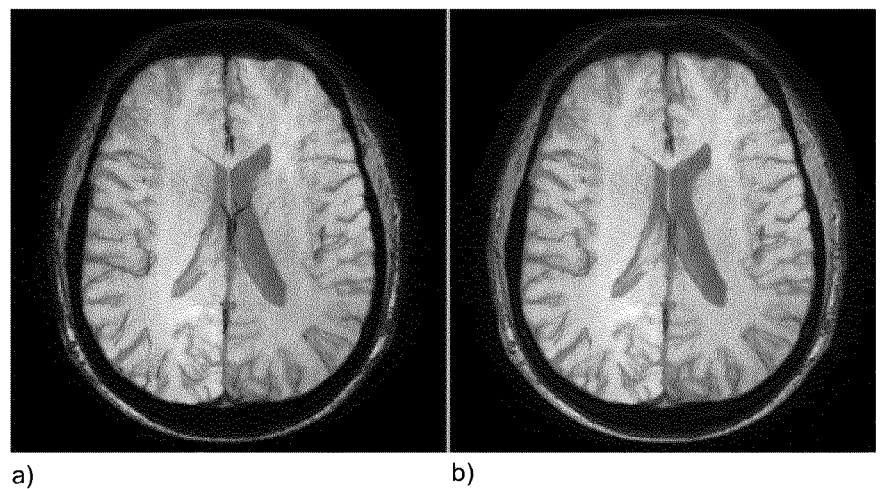
FIG. 2 shows in-vivo MR images acquired and processed according to the invention (a) and by conventional susceptibility weighted MR imaging (b)

The method of the invention provides a general basis for multi-echo susceptibility weighted imaging. It can advantageously be used for MR imaging of the brain. FIG. 2 shows the higher susceptibility contrast of the method of the invention compared with the conventional magnitude average method (as described, e.g., in US 2009/0251140 A1). FIG. 2a shows an in-vivo brain image acquired and processed by the method of the invention. FIG. 2b shows the same image acquired and processed with the conventional technique. Both images are displayed with the same intensity range and the same slab thickness (10 mm). A higher contrast and more details of the blood vessels can be observed in FIG. 2a.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method of magnet resonance (MR) imaging of an object placed in an examination volume of a MR device, the method comprising the steps of:
   a) with an MR scanner including a main magnet coil, a plurality of gradient coils and at least on RF coil, subjecting the object to an imaging sequence of radio frequency (RF) pulses and switched magnetic field gradients and acquiring echo signals;
   b) with at least one processor, controlling the MR scanner to excite resonance in the object and generate and acquire at least a first echo signal at a first echo time and a second echo signal at a second echo time;
   c) with the at least one processor controlling the MR scanner to repeat steps a) and b) to generate a plurality of first echo signals with each of a plurality of phase encoding steps and a plurality of the second echo signals with each of the plurality of phase encoding steps;
   d) with the at least one processor controlling the MR scanner to reconstruct a first intermediate MR image from the first echo signals with the first echo time and a second intermediate MR image from the second echo signals with the second echo time; and
   e) with the at least one processor controlling the MR scanner to generate a susceptibility weighted MR image by computing, for each voxel of the susceptibility weighted MR image, a non-linear combination of voxel values of corresponding voxels of the first and second intermediate MR images at each respective image position, wherein the non-linear combination emphasizes lower voxel magnitude voxel values more than higher voxel magnitude voxel values; and
   f) with a display device, displaying the susceptibility weighted MR image.

2. The method of claim 1, wherein the non-linear combination is computed by combining reciprocal values of the voxel values of the first and second intermediate MR images at each respective image voxel position.

3. The method of claim 2, wherein the step of generating the susceptibility weighted MR image comprises:

computing absolute values of the voxel values of the intermediate images at each respective intermediate image voxel position;
computing reciprocal values by raising each absolute value to a negative exponent; and
adding up, for each voxel of the susceptibility weighted MR image, the reciprocal values at each respective image voxel position.

4. The method of claim 3, wherein the step of generating the susceptibility weighted MR image further comprises a step of normalization of the combination of the reciprocal values at each image voxel position.

5. The method of claim 1, wherein the non-linear combination involves a computation of a weighted sum, wherein larger weighting factors are applied to voxel values of the intermediate images having a lower magnitude, while smaller weighting factors are applied to voxel values of the intermediate images having a higher magnitude.

6. The method of claim 5, wherein the intermediate MR images and the susceptibility weighted MR image are complex images.

7. The method of claim 1, wherein the intermediate MR images are magnitude images or susceptibility enhanced magnitude images.

8. The method of claim 1, wherein the imaging sequence is a multi-echo gradient echo sequence.

9. A magnetic resonance (MR) device comprising:
   at least one main magnet coil configured to generate a uniform, steady magnetic field (B0) within an examination volume;
   a plurality of gradient coils configured to generate switched magnetic field gradients in different spatial directions within the examination volume;
   at least one RF coil configured to generate RF pulses within the examination volume and/or to receive MR signals from an object positioned in the examination volume;
   one or more processors configured to control a temporal succession of RF pulses and switched magnetic field gradients, and reconstruct MR images from the received MR signals, wherein the one or more processors are further configured to:
   a) control gradient and RF coils to generate at least two echo signals at least at first and second echo times by subjecting the object to an imaging sequence of RF pulses and switched magnetic field gradients;
   b) acquire the echo signals at each of the at least first and second echo times;
   c) repeat steps a) and b) for a plurality of phase encoding steps;
   d) reconstruct at least a first intermediate MR image for the first echo time and a second intermediate image for the second echo time from the acquired echo signals; and
   e) generate a susceptibility weighted MR image by computing, for each voxel of the susceptibility weighted MR image, a non-linear combination of the voxel values at each corresponding voxel position of the at least first and second intermediate MR images, wherein the non-linear combination emphasizes lower voxel magnitude values more than higher voxel magnitude values.

10. The MR device of claim 9, further including a display device configured to display the susceptibility weighted MR image.

11. The MR device of claim 9, wherein the non-linear combination is computed by combining reciprocal values of the voxel values of the first and second intermediate MR images at each respective image voxel position.

12. The MR device of claim 11, wherein the one or more processors are further configured to:
   compute absolute values of corresponding voxels of the at least first and second intermediate images;
   compute reciprocal values by raising each absolute value to a negative exponent; and
   add for each voxel of the susceptibility weighted MR image, the reciprocal values.

13. The MR device of claim 12, wherein the one or more processors are further configured to:
   normalize the added reciprocal values of each voxel to generate the susceptibility generated weighted MR image.

14. The MR device of claim 9, wherein the one or more processors are further configured to:
   compute a weighted sum in which larger weighting factors are applied to voxel values of the intermediate images having a lower magnitude and smaller weighting factors are applied to voxel values of the intermediate images having a higher magnitude.

15. The MR device of claim 14, wherein the intermediate images and the susceptibility weighted MR image are complex images.

16. The MR device of claim 9, wherein the one or more processors are configured to control the plurality of gradient coils and the RF coil to:
   generate a multi-echo gradient echo sequence which generates more than two echo signals at additional echo times; and
   acquire echo signals at the additional echo times in addition to the first and second echo times.

17. The MR device according to claim 9, wherein a voxel value I of the susceptibility weighted MR image at each voxel position is defined by one of:

$$I = \sqrt[-p]{\frac{1}{N}\sum_{i=1}^{N} \|S_i\|^{-p}}, \, p > 0, \quad (1)$$

$$I = \frac{\sum_{i=1}^{N} \|S_i\|^{-p}}{\sum_{i=1}^{N} \|S_i\|^{-(p+1)}}, \, P > 0. \quad (2)$$

$$I = -\ln\left(\frac{1}{N}\sum_{i=1}^{N} \exp(-\|S_i\|)\right), \quad (3)$$

$$I = \frac{\sum_{i=1}^{N} \frac{S_i}{\|S_i\|^p}}{\sum_{i=1}^{N} \|S_i\|^{-p}}, \, p > 0, \quad (4a)$$

$$I = \frac{\sum_{i=1}^{N} S_i \exp(-\|S_i\|)}{\sum_{i=1}^{N} (-\|S_i\|)}, \quad (4b)$$

wherein N is the total number of echo time values, and $S_i$ represents the voxel values in the intermediate MR images attributed to the i-th echo value at the respective image voxel position.

18. A non-transitory computer readable storage medium having stored thereon a computer program to be run on a magnetic resonance (MR) device, which computer program comprises instructions for:
   a) executing an imaging sequence generating at least two echo signals at different first and second echo times;
   b) acquiring the echo signals;
   c) repeating steps a) and b) for a plurality of phase encoding steps;
   d) reconstructing at least a first intermediate MR image for the first echo time from the acquired echo signals and a second echo image for the second echo time; and
   e) generating a susceptibility weighted MR image by computing, for each voxel of the susceptibility weighted MR image, a non-linear combination of the voxel values of corresponding voxels of the at least first and second intermediate MR images, wherein the non-linear combination emphasizes lower voxel magnitude values more than higher voxel magnitude values.

19. The non-transitory computer-readable medium of claim 18, which further carries a computer program for controlling a display device to display the susceptibility weighted MR image.

* * * * *